United States Patent [19]
O'Brien et al.

[11] Patent Number: 6,152,929
[45] Date of Patent: Nov. 28, 2000

[54] METHOD AND APPARATUS FOR MEASURING HIP JOINT LAXITY

[75] Inventors: Robert T. O'Brien, Madison; Rudolf Dueland, Black Earth, both of Wis.

[73] Assignee: Wisconsin Alumni Research Foundation, Madison, Wis.

[21] Appl. No.: 09/064,587

[22] Filed: Apr. 22, 1998

[51] Int. Cl.[7] ................................................. A61B 17/56
[52] U.S. Cl. ............................................ 606/90; 600/231
[58] Field of Search ............................. 606/90; 600/220, 600/231, 232, 233, 243, 595

[56] References Cited

U.S. PATENT DOCUMENTS

| | | | |
|---|---|---|---|
| 4,344,420 | 8/1982 | Forder | 600/232 |
| 4,924,857 | 5/1990 | Mahmoodian | 600/220 |
| 5,482,005 | 1/1996 | Smith | 128/782 |

OTHER PUBLICATIONS

O'Brien, et al., Dynamic Ultrasonographic Measurement of Passive Coxofemoral Joint Laxity in Puppies:, *J. Am. Anim. Hosp. Assoc.* 33: 275–281 (1997).

Smith et al., "New Concepts of Coxofemoral Joint Stability and the Development of a Clinical Stress–Radiographic Method for Quantitating Hip Joint Laxity in the Dog", *JAVMA* 196: 59–70 (1990).

Smith et al., "Coxofemoral Joint Laxity from Distraction Radiography and its Contemporaneous and Prospective Correlation with Laxity, Subjective Score, and Evidence of Degenerative Joint Disease from Conventional Hip–Extended Radiography in Dogs", *Am. J. Vet. Res.* 54: 1021–42 (1993).

Saies et al., "The Value of a New Ultrasound Stress Test in Assessment and Treatment of Clinically Detected Hip Instability", *J. Ped. Ortho.* 8: 436–441 (1988).

Harcke et al., "Performing Dynamic Sonography of the Infant Hip", *AJR* 155: 837–844 (Oct. 1990).

Corley et al., "Hip Dysplasia—A Progress Report and Update", *OFA* (1993 Supplement).

O'Brien et al., "Ultrasound Diagnosis of Hip Dysplasia in Two Litters of Puppies", Veterinary Orthopedic Society Twentieth Annual Conference, Lake Louise, Alberta, Canada, Feb. 27–Mar. 6, 1993.

Trout et al., "A Prospective Study of Canine Hip Dysplasia Using Ultrasound: A Preliminary Report", Europ. College of Veterinary Surgeons Second Scientific Annual Meeting, Cambridge, England, Jun. 2–4, 1993, Abstract No. 16.

Moore, "Canine Medical Information, Part II", http://www.k9web.com/dog–faqs/medical/medical~info.02.html, 1996.

Davel, "Canine Hip Dysplasia: Are Breeders Winning the Battle?", http://home.ici.net/~jiminma/dysp2.htm, date unknown.

Cargill et al., "Canine Hip Dysplasia Part I, II, III, IV, V, VI, VII and VIII", http://www.acmepet.com/canine/genetic/article, date unknown.

International Canine Genetics, "Questions and Answers about PennHIP: A New Scientific Method for Early Screening for Canine Hip Dysplasia", http://www.cis.ohio–state.edu/hypertext/faq/usenet/dogs–faq/medical–infor/pennhip/faq.html, 1996.

Evans, H.E. and Christensen, G.C. "Miller's Anatomy of the Dog", 2nd Edition pp. 197–209, 256–257, WB Saunders, Philadelphia, 1979.

*Primary Examiner*—Michael Buiz
*Assistant Examiner*—Julian W. Woo
*Attorney, Agent, or Firm*—Quarles & Brady LLP

[57] ABSTRACT

An apparatus is employed to determine hip joint laxity in canines. The apparatus, which is adjustable for the size of the canine, is placed between the thighs of a canine patient in ventral recumbency, the pelvic limbs are manipulated to compress or distract the coxofemoral joint and the compression or distraction is imaging by non-radiographic means.

14 Claims, 5 Drawing Sheets

$(4-2)-(3-1)=$ distraction distance

METHOD AND APPARATUS FOR MEASURING HIP JOINT LAXITY

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Hip dysplasia is a potentially debilitating disease in dogs with a breed-related incidence reaching seventy percent or higher. Using existing methods, dogs are not determined to be free of hip dysplasia until two years of age. Recent work has demonstrated the utility of stress radiography to diagnose passive hip laxity in puppies as young as four months of age. Smith, G. K. et al., "New Concepts of Coxofemoral Joint Stability and the Development of a Clinical Stress-Radiographic Method for Quantitating Hip Joint Laxity in the Dog," *JAVMA* 196:59–70 (1990) and Smith, G. K. et al., "Coxofemoral Joint Laxity from Distraction Radiography and Its Contemporaneous and Prospective Correlation with Laxity, Subjective Score, and Evidence of Degenerative Joint Disease from Conventional Hip-Extended Radiography in Dogs," *Am. J. Vet. Res.* 54:1021–42 (1993).

Ultrasonography has been used to diagnose human hip dysplasia since the early 1980s. Initially, ultrasonography was used to describe morphological characteristics related to the coxofemoral joint components. Ultrasound techniques measure the distance traveled by the head of the femur from compression to distraction of the hip joint. Manual compression and distraction are not always adequate to diagnose hip laxity in young dogs because varying results arise from differences in techniques and strength of the clinician.

Recently, diagnostic ultrasound has also been advantageously employed to image the coxofemoral joint and to diagnose hip laxity in puppies. Ultrasonic imaging during manual compression and distraction of the coxofemoral joints of dogs placed in ventral recumbency was described by O'Brien, R. T. et al., "Ultrasound Diagnosis of Hip Dysplasia in Two Litters of Puppies," Veterinary Orthopedic Society Twentieth Annual Conference, Lake Louise, Alberta, Canada, Feb. 27–Mar. 6, 1993. A more extensive report by the same researchers was published at O'Brien, R. T., et al., "Dynamic Ultrasonographic Measurement of Passive Coxofemoral Joint Laxity in Puppies," *J. Am. Anim. Hosp. Assoc.* 33:275–381 (1997). A shortcoming of the O'Brien et al. method is that it, like the Smith method, requires two clinicians, one of which positions the pelvic limbs while the second obtains the images.

See also Trout, N. J. et al., A Prospective Study of Canine Hip Dysplasia Using Ultrasound: A Preliminary Report," *Europ. College of Veterinary Surgeons Second Scientific Annual Meeting*, Cambridge, England Jun. 2–4, 1993, Abstract No. 16 and Harcke, H. T. and L. E. Grissom, "Performing Dynamic Sonography of the Infant Hip," *A Jr.* 155:837–844 (October 1990) and Saies, A. D., "The Value of a New Ultrasound Stress Test in Assessment and Treatment of Clinically Detected Hip Instability," *J. Ped. Ortho.* 8:436–441 (1988).

Specialty instruments can assist in the hip distraction process. U.S. Pat. No. 5,482,055 (Smith) describes a method and apparatus for determining hip joint laxity in a dog. Smith describes a method for determining hip joint laxity in which radiographic images of the hip joint in compression and distraction are compared using a gauge to determine a distraction index. The dog, which can be only as young as about sixteen weeks, is placed in dorsal recumbency and the hips are manipulated as described. Smith also describes an apparatus for distracting the hips. However, the apparatus can only be used on a dog placed in dorsal recumbency and requires one clinician to manipulate the apparatus and a second clinician to obtain the radiographic images.

A method for determining coxofemoral joint laxity in puppies by a single clinician is still not known in the art. Therefore, what is desired is a method for distracting and for measuring distraction that can be accomplished by a single clinician. An apparatus suitable for use in such a method would also be desired.

BRIEF SUMMARY OF THE INVENTION

The present invention is a method for evaluating coxofemoral joint laxity in puppies. The method is summarized in that a young canine patient (about four to twenty-six weeks of age) is placed in ventral recumbency (prone). A distractor is positioned in the patient's upper thigh region so that the distractor serves as a fulcrum for lateral displacement (distraction) of the hips. Gentle pressure is then applied to the knee (stifle) region of both legs to achieve distraction. The distractor is then removed and the legs are then pulled gently together to achieve hip compression. In the method, an image acquisition device can be used to obtain images of the coxofemoral joints in distraction and in compression.

As only a single hand is required to manipulate the patient into distraction and compression, a second, or imaging, hand is free to operate the image acquisition device. A clinician can support the distractor with one hand and with the same hand can apply inward pressure to the stifle region to achieve distraction. During compression, one hand can be placed on the upper thigh region of both legs so that the fingers of the non-imaging hand wrap around one leg while the thumb of that same hand wraps around the opposite leg. In each case, a second hand is not required for manipulation. Thus while the method can be performed by more than one clinician, only one clinician is required.

The present invention is also summarized in that a distractor suitable for distracting the hips of young puppies in the method of the present invention includes two generally parallel end members joined by two generally parallel side bars. One side bar can be rigidly fixed at one end of the end members while the second side bar can be slidably mounted between the end members. The slidable side bar can be secured at a desirable distance from the fixed side bar to accommodate use with patients of various sizes.

It is an object of the present invention to provide a method and apparatus that allows a single clinician to acquire images of each hip in compression and distraction for subsequent analysis.

It is another object of the present invention to provide a method and apparatus that is suitable for use on puppies as young as six to eight weeks of age.

It is a feature of the present invention that images of both hips can be acquired with a single manipulation.

It is another feature of the present invention that a suitable distractor includes generally rectangular-shaped side bars on its side, rather than the rods of the prior art apparatus. The non-round shape of the side bars ensures that the apparatus does not dislodge or slip out from between the thighs while measuring compression and distraction. Pressure on the outer sides of the side bars by the patient's femurs holds the apparatus in place. The prior art apparatus of Smith would be inappropriate in the present method because it would slip out from between the thighs.

It is an advantage of the present invention that the clinician need not apply downward force with two hands to achieve distraction, as was the case with the Smith method and apparatus. Instead, in the present method, one supports the apparatus while the second hand is available to operate the image acquisition device.

It is another advantage of the present invention that the method and apparatus can be advantageously employed in clinics having only a single clinician.

It is yet another advantage of the present invention that the acquired images can be non-radiographic images, such as sonographic images, which are easier, safer, and less expensive to acquire than radiographic images that have been required in other methods for evaluating coxofemoral joint laxity.

Other objects, advantages and features of present invention will become apparent upon consideration of the following detailed description taken in conjunction with the accompany drawings.

DETAILED DESCRIPTION OF THE INVENTION

Figure 1:
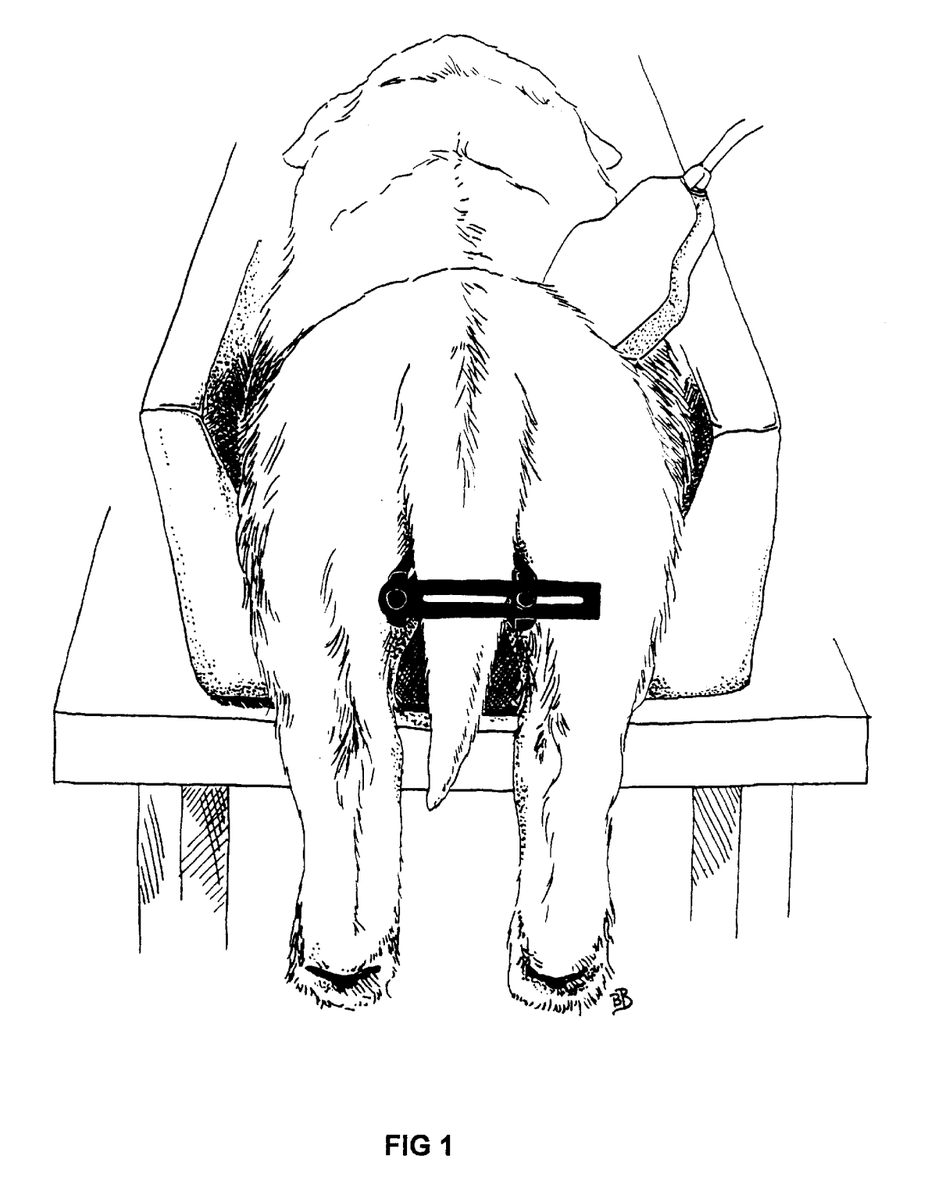
FIG. 1 depicts positions of a distractor and an image acquisition device in a method for distracting as described.

The distraction portion of the method is shown in FIG. 1. In the method of the present invention, a clinician places a distractor between the upper thighs of a canine patient in ventral recumbency so that the distractor contacts the inner thighs of the patient. The weight of the dog's hind quarters and abdomen should rest on the device. With the device in place, the clinician can support the device with one hand (the "manipulating hand" or "non-imaging hand") to prevent the device from tilting relative to the legs. The device should be positioned as proximal (toward the hip joint portion of the femurs) as is allowed by the weight of the dog and the interposed tissues of the ventral abdomen. No additional forces need to be applied to the device to ensure that the device is appropriately positioned close to the hips. With the same hand, can apply inward pressure to the knee (stifle) region of both legs to achieve distraction. In clinical use, the imager usually needs a firm grasp of the device to prevent the device from tilting as force is applied to the stifles. While maintaining the inward pressure, the clinician can use the second hand (the "imaging hand") to position an image acquisition device to obtain non-radiographic images of the coxofemoral (hip) joints in distraction.

The image acquisition device is preferably a non-radiographic device, and is typically an ultrasonic transducer (such as a 7.5-Mhz ultrasound transducer such as SI450, Siemens Quantum, Inc., Issaquah, Wash.). A modified dorsal view provides the best sonographic plane to image the components of the coxofemoral joint and to allow measurement of the distance moved between compression and distraction. The dorsal plane of the hip is a long axis view with the transducer directed from the side (i.e., left to right in the left hip). From this initial plane, the transducer can be rotated slightly (i.e., clockwise in the left hip) so that the cranial aspect of the transducer is more dorsal than the caudal portion. The desired end result is an image in which the cranial-dorsal ilium appears to form a horizontal straight line and the rounded femoral head is seen well. In this position, the transducer needs only subtle adjustment to maintain the same image plane during compression and distraction maneuvers. With practice, both hips can be evaluated, and images can be collected, within ten minutes.

It is not absolutely essential that the patient's hair be clipped at the transducer site, especially with young (six to eight week old) puppies. Good quality images can be obtained through the hair coat by applying copious isopropyl alcohol and acoustic gel.

To compress the hip joints, the device is removed and the legs can then be gently pulled together. It is preferred that the clinician wraps the fingers of the manipulating hand around one leg at the upper thigh while the thumb of the same hand wraps around the opposite leg, whereupon the images of the coxofemoral joints in compression can be obtained in the same manner as was described above.

Distraction should be performed first. The movement from distraction to compression is less stressful to the patient, resulting in a lower possibility of the patient moving. The hips should be distracted, an image collected, and then the hips placed into compression. The second, and final, image is then collected in compression.

In the experience of the inventors, the highest quality images of the components of the coxofemoral joint were obtained in puppies between six and sixteen weeks of age although an age range of about 4–26 weeks can be suitable. It is preferred that the analysis be performed before the age at which the femoral heads are surrounded by a mineralized acetabular rim.

After acquiring the images of each hip in compression and distraction, preferably on split-screen images, the distracted distance is measured. In a first preferred method for determining the distracted distance, the images are digitized, and the compression and distraction images are merged ("blended") using image analysis software capable of blending two images (such as NIH Image 1.60 or subsequent current version (http://rsb.info.nih.gov/nih-image/download.html; see FIGS. 3a,b of O'Brien, supra (1997) for example of such a blended image). This analytical method has certain shortcomings in that it requires a separate computer and specialized software to perform the time consuming and technically challenging process of image blending. Moreover, the ultrasound image must be converted from the proprietary data format of the device manufacturer to a conventional format such as PICT or TIFF.

Figure 2:
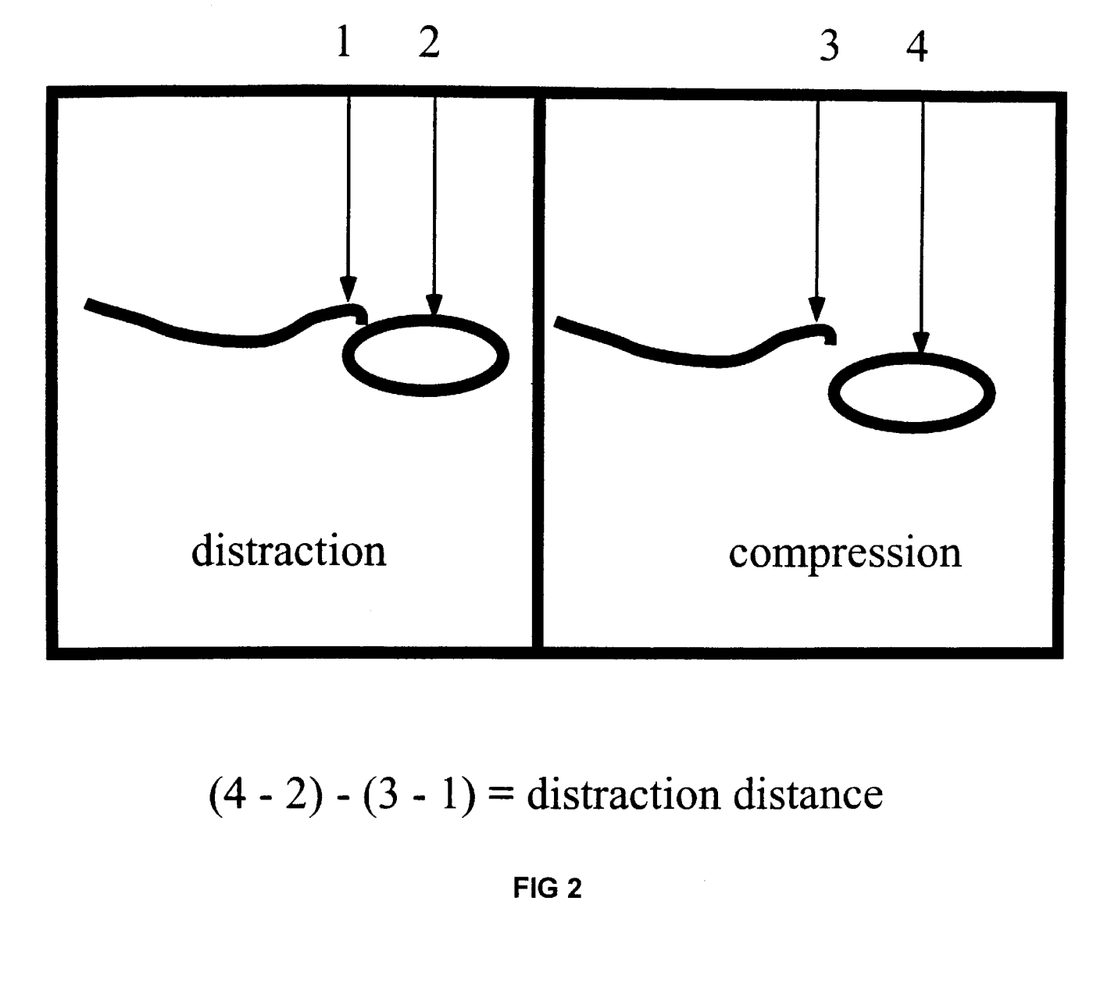
FIG. 2 summarizes four measurements needed to determine distraction distance in a preferred embodiment of a method of the present invention.

Alternatively, a simply mathematical formula that corrects for differing sized fields of view using a conversion factor (pixel per millimeter), provides the distraction distance when four points are identified on the images. On each image, the position of the skin is known. In addition, the highest points on both the cranial dorsal acetabular rim and the femoral head are identified. From these points, the distraction distance can be determined and normalized. In this approach, four measurements are necessary from a common reference point, such as the top of the screen or image border:

1. caudal-most point of acetabular rim (with hip in distraction);
2. lateral-most point of femoral head (with hip in distraction);
3. caudal-most point of acetabular rim (with hip in compression); and
4. lateral-most point of femoral head (with hip in compression).

Using these four measurements (summarized in FIG. 2), the distraction distance is determined from the formula (distance 4–distance 2)–(distance 3–distance 1).

All measurements should be drawn with a straight vertical line and the reference points should be consistent between compression and distraction images, especially on the acetabulum rim measurements. If image measurements are taken from paper images, rather than analyzed on the ultrasound machine, the calculated distraction distance must be multiplied by a proportionality factor that can be determined by comparing the known length of a line on the ultrasound image against the length of the same line on the paper image. For example, if a 3 cm line on the ultrasound image measures 2 cm on the paper image, then the proportionality factor is 0.667.

Figure 3:
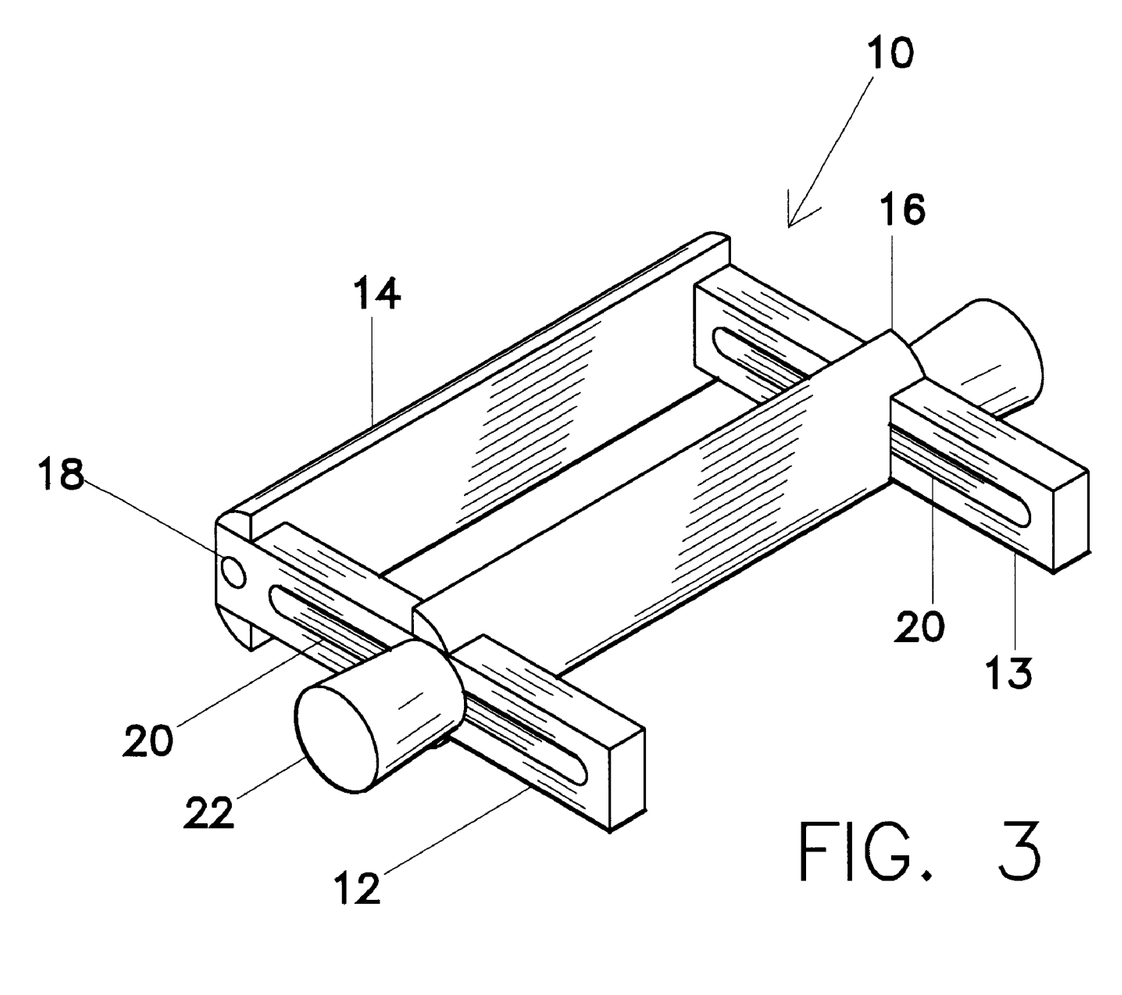
FIG. 3 depicts a second preferred embodiment related to a preferred embodiment of a distractor made in accordance with the present invention.
Figure 4:
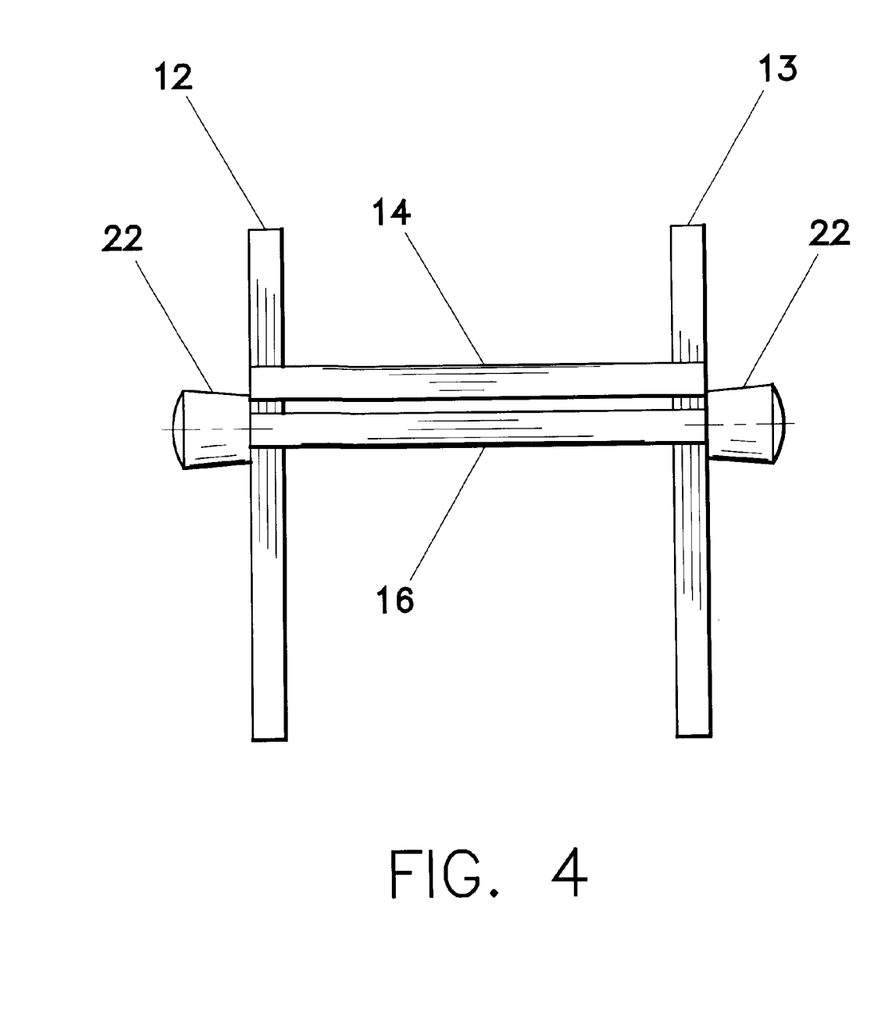
FIG. 4 depicts a second preferred embodiment related to the distractor of FIG. 3 in top view.
Figure 5:
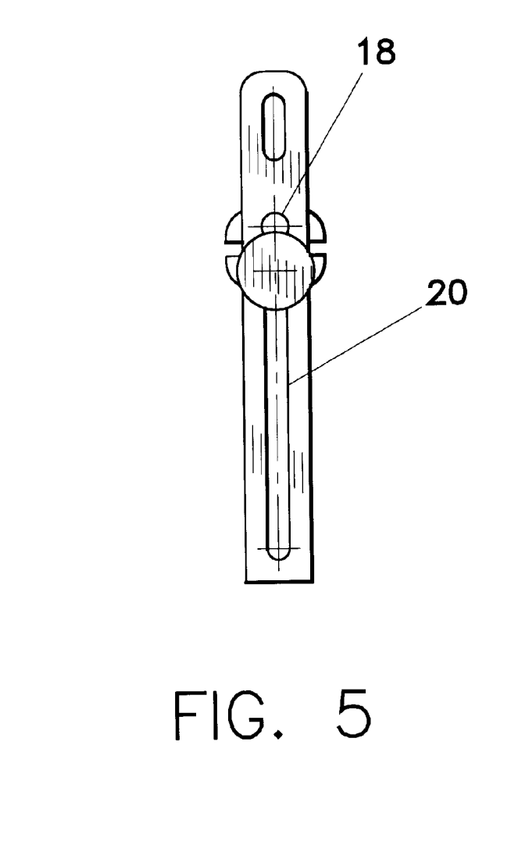
FIG. 5 depicts the distractor of FIG. 3 in side view.

In a second aspect, the present invention is a distractor that, when placed between the upper thighs of the canine patient, serves as a fulcrum for laterally displacing (distracting) the hips. FIG. 3 depicts a preferred distractor. In this application, inner and outer, top and bottom refer to positions relative to the center of the distractor of FIG. 3.

A preferred distractor 10 includes a pair of end means 12 and 13, each of which is generally rectangular in shape with an inner face and an outer face. The distractor 10 also includes a pair of generally rectangular spaced apart side bars 14 and 16 mounted perpendicularly to the end members. The end means 12, 13 and the side bars 14, 16 can be solid or hollow and can be made of any rigid material such as hard plastic or Lucite. A portion of each of the side bars 14 and 16 along its short side edges is recessed, to receive the end members 12 and 13. The side bars 14 and 16 should include outward facing sides that are sufficiently large to permit the apparatus to act as a fulcrum during distraction and to permit the clinician to support the distractor with one hand in the method.

Optional modifications to the surface of the apparatus can be provided, such as means for supporting the apparatus in use. In the preferred embodiment, side bars 14 and 16 are not strictly speaking rectangular since each includes a pair of rounded edges toward the outer face to enhance the comfort of the canine patient during distraction. The edges toward the inner face can also be rounded, although the general shape of the side bars 14 and 16 should be rectangular, as opposed to cylindrical, and the outer faces should be generally flat. The extent to which the outer edges of side bars 14 and 16 are curved is not essential to the invention, however, some curvature is preferred. The outer faces of side bars 14 and 16 can be provided with textural indicia to further discourage slippage in use.

Side bars 14 and 16 are in mirror image orientation relative to each other in the distractor 10. That is, the outside edges of side bars 14 and 16 each face the outside of the apparatus while the inside edges face toward each other and toward the inside of the distractor 10. Side bar 14 can be fixedly connected to the end members. The connection can be by attachment means 18, such as a screw, as is shown in FIG. 3, or by adhesive connection. In an alternate construction, a single element can comprise the pair of end means 12 and side bar 14. Side bar 16 can be slidably mounted to the end members 12 and 13. In the preferred embodiment, a slot 20 is defined through each end member 12, 13. The slots 20 permit the distance between side bars 14 and 16 to be adjusted. End caps 22 provided at each end of side bar 16 pass through the slots. The end caps may be loosened to permit lateral adjustment of side bar 16 relative to end members 12 and 14, and then tightened to prevent further change in the distance between side bars 14 and 16 during use of the apparatus 10.

The distance between side bars 14 and 16 can vary with the size of the dog, as long as when the distractor 10 is in place it can act as a fulcrum on the femurs. The optimal distance between side bars 14 and 16 is between about 3.5 and 4.5 cm for puppies that are sized like a 6–8 week-old Labrador or Golden Retriever. In use, the slidable side bar 16 is adjusted laterally relative to end members 12 and 13 so that side bar 16 is spaced apart from side bar 14 at a distance such that when the hips are maximally distracted, the stifles are within one to two cm of each other, but not touching. Given the variation within typical litters of puppies, the device is usually adjusted only once, at the beginning of imaging.

It is, of course, understood that the relationships between the end members 12 and 13 and the side bars 14 and 16 need not necessarily be exactly rectangular. However, a rectangular fit among the parts is preferred as that arrangement facilitates a stable apparatus with minimal structural requirements. Other arrangements that meet these general structural requirements are intended to fall within the scope of the present invention. In a related embodiment, the spaced apart relation between the side bars 14, 16 can be a fixed distance, if the distractor is to be used for only canines of a particular size. Indeed, the entire distractor can be formed as a single part, since no movement of any element is required in use.

The present invention will be better understood upon consideration of the following Examples which are intended to be exemplary and not limiting on the invention.

EXAMPLE

Figure 6:
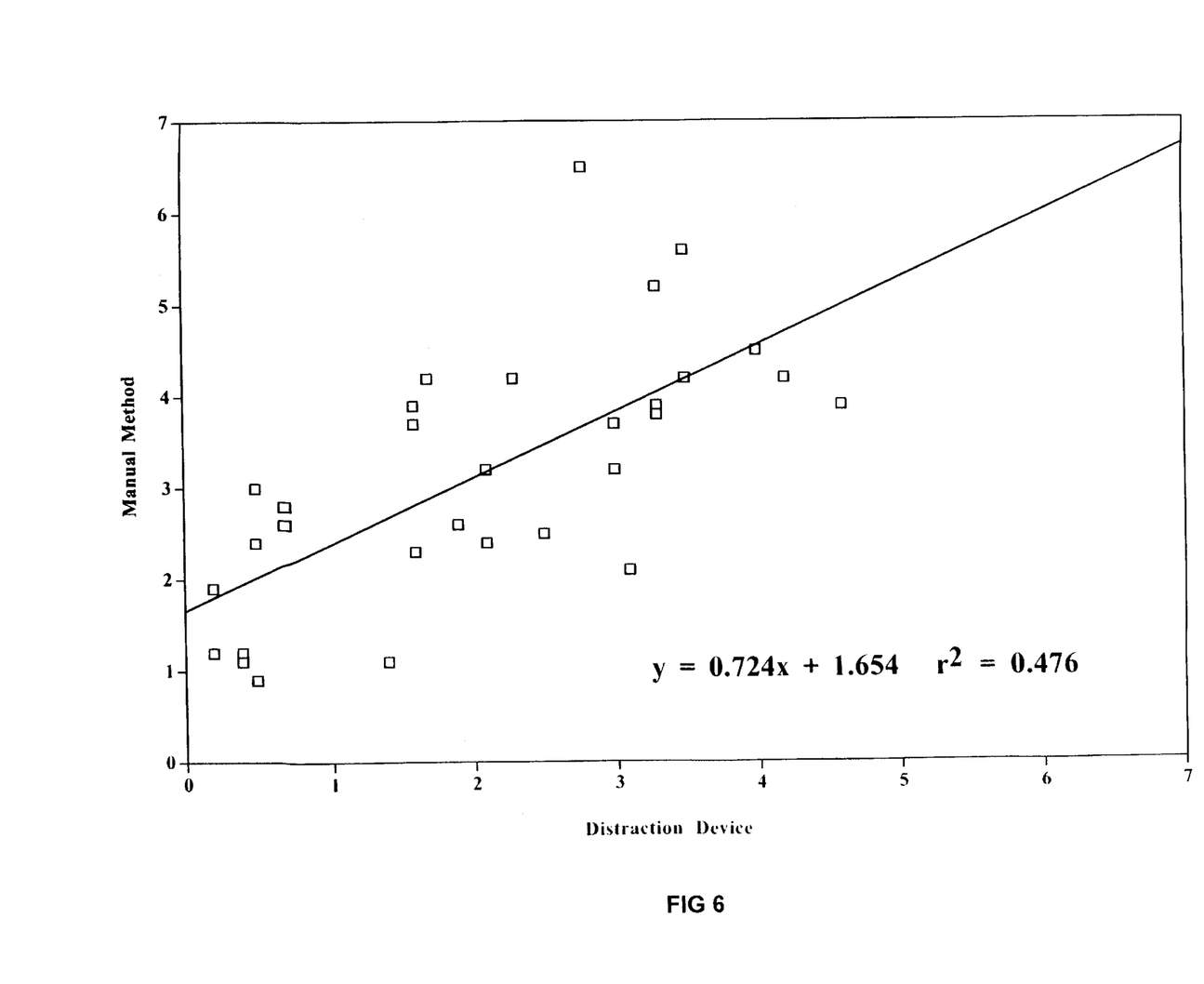
FIG. 6 depicts data obtained when a distractor prepared in accordance with the present invention was tested in the method of the present invention on 30 puppy hips. The results indicate an association between distraction distances measured using the manual method and those measured using the distraction device.

A distractor prepared in accordance with the invention was tested using the method of the present invention on 30 puppy hips. The distraction distance was also determined using existing manual methods. The data of FIG. 6 demonstrate an association between distraction distances measured using the distractor and those obtained using manual methods.

The invention is not intended to be limited to the foregoing Examples, but rather to encompass all such variations and modifications as come within the scope of the appended claims.

We claim:

1. A distractor for distracting a coxofemoral joint, the distractor comprising:

two end panels, each having a long axis; and first and second spaced apart generally parallel, non-round side bars securable at about right angles to the end panels, each side bar having an outer face, the first side bar being fixedly secured to the end panels, the second side bar being movably securable to the end panels.

2. A distractor as claimed in claim 1, the outer faces of the side bars comprising textural indicia thereupon.

3. A distractor as claimed in claim 1, the outer faces of the side bars comprising at least one rounded edge.

4. A distractor as claimed in claim 1 wherein the first and second spaced apart non-round side bars have a variable distance therebetween and the movably securable side bar being movable along the long axis of the end panels.

5. A distractor as claimed in claim 4 wherein each end panel has a slot passing therethrough, the slot being parallel to the long axis.

6. A distractor for distracting a coxofemoral joint, the distractor comprising:

at least one end panel having a long axis; and first and second spaced apart generally parallel, non-round side bars securable at about right angles to the at least one end panel, each side bar having a generally flat outer face, the outer faces of the side bars comprising at least one rounded edge having a long axis at about a right angle to the long axis of the end panel.

7. A distractor as claimed in claim 6 wherein the first and second side bars are longer than the at least one end panel.

8. A distractor as claimed in claim 6 wherein the first side bar is fixedly secured to the at least one end panel.

9. A distractor as claimed in claim 6, the outer faces of the side bars comprising textural indicia thereupon.

10. A distractor as claimed in claim 6 comprising two end panels, both side bars being securable to the end panels.

11. A distractor as claimed in claim 10, the first side bar being fixedly secured to the end panels, the second side bar being movably securable to the end panels.

12. A distractor as claimed in claim 6 wherein the first and second spaced apart non-round side bars have a variable distance therebetween and at least one side bar is movably securable to the at least one end panel, the at least one movably securable side bar being movable along the long axis of the at least one end panel.

13. A distractor as claimed in claim 6 wherein the at least one end panel has a slot passing therethrough, the slot being parallel to the long axis.

14. A distractor as claimed in claim 13 wherein the first and second spaced apart non-round side bars have a variable distance therebetween and at least one side bar is movably securable to the at least one end panel, the at least one movably securable side bar being slidable along the slot passing through the at least one end panel.

\* \* \* \* \*

UNITED STATES PATENT AND TRADEMARK OFFICE
CERTIFICATE OF CORRECTION

PATENT NO. : 6,152,929
DATED : November 28, 2000
INVENTOR(S) : Robert T. O'Brien and Rudolf Dueland It is certified that error appears in the above-identified patent and that said Letters Patent is hereby corrected as shown below:

Column 1,
Line 6, delete "Not applicable." and insert:

-- This invention was made with United States government support awarded by the following agency:

NOAA Grant Number NA46RG0481.

The United States government has certain right in this invention. --

Signed and Sealed this

Third Day of December, 2002

JAMES E. ROGAN
*Director of the United States Patent and Trademark Office*